US006703034B2

(12) United States Patent
Parmar et al.

(10) Patent No.: US 6,703,034 B2
(45) Date of Patent: Mar. 9, 2004

(54) NEEM OIL MICROEMULSION WITHOUT COSURFACTANTS OR ALCOHOLS AND A PROCESS TO FORM THE SAME

(75) Inventors: Balraj S. Parmar, New Delhi (IN); Manoj Varshney, New Delhi (IN); Dinesh O. Shah, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 10/016,243

(22) Filed: Dec. 10, 2001

(65) Prior Publication Data

US 2002/0091164 A1 Jul. 11, 2002

Related U.S. Application Data

(60) Provisional application No. 60/254,714, filed on Dec. 11, 2000.

(51) Int. Cl.⁷ ................................ A01N 25/04; B01F 3/08; B01F 17/42
(52) U.S. Cl. ..................... 424/405; 516/76; 424/761; 514/453; 514/938; 106/504
(58) Field of Search ............... 516/66, 76; 424/761, 424/405; 514/453, 938; 504/363; 106/504

(56) References Cited

U.S. PATENT DOCUMENTS 4,704,220 A * 11/1987 Goddard et al. ............ 516/76
5,110,591 A * 5/1992 Williams .................... 424/761
5,334,585 A * 8/1994 Derian et al. .............. 514/941
5,374,614 A * 12/1994 Behan et al. ............... 512/4
5,733,847 A * 3/1998 Heinrich et al. ........... 504/363
5,792,465 A * 8/1998 Hagarty ..................... 514/937
6,045,816 A * 4/2000 Narayanan et al. ........ 514/937

OTHER PUBLICATIONS

Shinoda et al., Emulsions and Solubilization (John Wiley & Sons, NY, NY, Copyright 1986), pp. 95–101 and 122–124 (Apr. 1987).*

* cited by examiner

Primary Examiner—Daniel S. Metzmaier
(74) Attorney, Agent, or Firm—Akerman Senterfitt

(57) ABSTRACT

A method of forming an oil in water microemulsion includes the steps of providing at least one non-ionic ethoxylated surfactant, providing an oil and mixing the surfactant and the oil to form a microemulsion. The surfactant can be selected from the group of alkyl phenol ethoxylates, where the alkyl group contains 8 to 12 carbons and the ethoxylate contains an average of 4 to 12 ethoxylate groups. The surfactant can be a nonyl phenol ethoxylate. An oil in water microemulsion includes at least one non-ionic ethoxylated surfactant and at least one oil. The surfactant can be a single surfactant or a mixed surfactant. The oil can be derived from at least one tree, preferably from as the Neem Tree.

15 Claims, No Drawings

NEEM OIL MICROEMULSION WITHOUT COSURFACTANTS OR ALCOHOLS AND A PROCESS TO FORM THE SAME

CROSS REFERENCE TO RELATED APPLICATIONS

This application claims the benefit of U.S. Provisional Application No. 60/254,714 entitled, "NEEM OIL MICROEMULSION WITHOUT COSURFACTANTS OR ALCOHOLS AND A PROCESS TO FORM THE SAME" filed Dec. 11, 2000, the entirety of which is incorporated herein by reference.

BACKGROUND OF THE INVENTION

The Indian Neem Tree (*Azadirachta indica* A. Juss) has been recognized as a promising source of a plurality of biologically active chemicals, finding applications in diverse areas of utility to mankind. Neem Oil is obtained mainly from its seeds and may be obtained by press or solvent extraction from Neem seeds/kernels. Neem Oil consists primarily of fatty acids and meliacins. The latter, in particular, have been established to be bio-active. The principal meliacin, azadirachtin-A, has been reported to be present in different oils ranging from non-detectable to about 2500 parts by weight per million parts of the oil.

Neem Tree derivatives are used widely in agriculture, consumer products, human and veterinary medicine, insecticides as well as other areas. Derivatives from the Neem Tree have been shown to rejuvenate, detoxify and purify the skin of humans. For example, Neem Oil derived from Neem leaf and Neem bark have been reported to be effective for treatment of cuts, bruises, skin disorders and acne, and as a cosmetic to remove skin blemishes. Neem Oil also has a large number of medical applications and is reportedly effective for treating psoriasis. It has been shown to be antimalarial, antitubercular, antiviral, antiallergic antigingvitic, antiperiodonitic antiseptic, antimicrobial and antihyperglycemic. Neem Oil has been shown to be an effective analgesic, especially for earaches and headaches. It is also effective in controlling diabetes. Neem leaf is regarded as a traditional herb for treating diabetes and has been specifically proven to be effective in preventing and treating diabetes.

Neem Oil has been reported to be an effective insecticide. Entomologists have isolated approximately 390 different insect species that are controlled by the bio-activity of chemicals described from the Neem Tree. Several of these insect species are resistant to chemical pesticides or are inherently difficult to control. However, as the chemical composition of the meliacins of Neem Oil are extremely complex, thus far there are no recorded cases of insect pests having developed a resistance to Neem Oil.

When ingested by insects, Neem Oil creates hormonal disruptions which prevent the insect from feeding, breeding or metamorphosing. As a pesticide, the United States EPA has exempted Neem Oil from the requirement of tolerance (Federal Register: Dec. 13, 1995, Volume 60, number 239).

The main active ingredient of Neem Oil, azadirachtin, exhibits antifeedant, insect repellent and insect sterilization properties. It is potent at quantities as low as 1 ppm which can repel certain insects. Neem Oil interferes with ecdysone, the key insect molting hormone and prevents insect larvae and pupae from completing the molting process.

Insects treated with azadirachtin during the larval and pupal stages, which comprise approximately 60–70% of their lives, generally die within 3–14 days. Unlike chemical insecticides em Oil works on the insect's hormonal system, not on the digestive or nervous system. Accordingly, Neem Oil does not lead to development of resistance in future insect generations and is recognized as an effective insect antifeedant and repellent. But better results can be obtained by using all meliacins together. A kind of synergistic effect is obtained whereby one component strengthens and increases the working of another.

Neem Oil has also been shown to be a useful lubricant and fuel additive. For consumer applications, Neem Oil is used in various toiletry preparations such as soaps, shampoos, dental and mouth hygiene items, cosmetics, and other personal care products.

Neem Oil can be dispensed directly or incorporated into various products. Neem Oil is generally used either in a solution, in an organic solvent or in various forms of dispersions, such as emulsions, suspensions, etc. The direct use of Neem Oil poses problems of non-uniform distribution. The use of organic solvents, besides being costly, can introduce fire and the toxicity hazards. Moreover, currently used dispersions are usually unstable. For example, a typical Neem Oil emulsion may have an average particle diameter in the range of 0.2 to 50 micrometers ($\mu$m). These emulsions quickly separate into the Neem Oil and the aqueous phases upon standing, often in periods measured in hours.

Thus, a need exists for alternative methods of dispensing oils such as Neem Oil for various applications such as soaps, shampoos, cosmetics and other personal care products, medical and public health products, pesticidal sprays and fertilizer coats.

The development of microemulsion technology has enabled formation of improved dispersions for some materials. Microemulsions are thermodynamically stable dispersions of one liquid phase into another, stabilized by an interfacial film of surfactant. This dispersion may be either oil-in-water or water-in-oil. Microemulsions are typically clear solutions, as the droplet diameter is approximately 100 nanometers or less. The interfacial tension between the two phases is extremely low.

Emulsions (or macroemulsions) are in contrast unstable. The suspended droplets will eventually agglomerate and the dispersed phase will phase separate. Emulsion droplet sizes are much larger, typically one micron or more, resulting in a cloudy or milky dispersion. The nature of an emulsion may depend on the order of mixing of the ingredients and the amount of energy put into the mixing process. The final microemulsion state will not depend on order of mixing, and energy input only determines the time it will take to reach the equilibrium state. There have been limited efforts to develop Neem Oil dispersions, including microemulsions. For example, U.S. Pat. No. 5,110,591, to Williams, discloses a concentrated water-in-oil Neem Oil microemulsion containing a pesticidally effective amount of azadirachtin formed as a concentrated emulsion. Upon dilution with water, the concentrate forms storage stable oil-in-water emulsions. In U.S. Pat. No. 5,792,465 to Hagerty, microemulsions containing insecticides or other insect control agents including Neem Oil, and methods for their use are disclosed. The disclosed microemulsions have above 20% hydrocarbon, and use less than about 7.5% emulsifier, weight by weight of the final product. The microemulsions can be delivered in aerosol form using a hydrocarbon propellant. Although both of the above patents describe oil dispersions, each employ a complex surfactant system and/or alcohols as a co-surfactant and are accordingly complex and expensive to prepare as well as potentially harmful to the environment.

It is desired to develop a Neem Oil microemulsion which is co-surfactant and alcohol free. In addition, it would be desirable to develop a Neem Oil microemulsion that is simpler, safer and more environment friendly.

SUMMARY OF THE INVENTION

A method of forming an oil in water microemulsion includes the steps of providing at least one non-ionic ethoxylated surfactant, providing an oil and mixing the surfactant and the oil to form a microemulsion. The surfactant can be a single surfactant. The oil in the microemulsion can vary from 0.001 to 5%, weight by weight of the final product (w/wf). The oil droplet size can range from approximately 5 nm to 80 nm. The microemulsion may be used for a variety of applications, such as cosmetics, toiletries, paints, varnishes, agrochemicals, medicines and pesticides.

The surfactant can be selected from the group of alkyl phenol ethoxylates, where the alkyl group contains 8 to 12 carbons and the ethoxylate contains an average of 4 to 12 ethoxylate groups. The surfactant can be a nonyl phenol ethoxylate.

The surfactant can be a mixed surfactant. In one embodiment, the surfactant includes nonyl phenol ethoxylate and an ionic surfactant. In this embodiment, the ionic surfactant can be alkyl benzene sulfonate and the surfactants comprise 0.003 to 25% w/wf. The surfactant to oil ratio in this embodiment is preferably at least 3:1. The mixed surfactant can also include at least one alkyl alcohol having 1 to 7 carbons.

The oil can vary from 5 to 15% w/wf, whereby a concentrate can be formed. Concentrates can be later diluted prior to application. In this embodiment, surfactants preferably total 15 to 60% w/wf.

An oil in water microemulsion includes at least one surfactant selected from the group consisting of non-ionic ethoxylated surfactants and at least one oil. The surfactant can be a single surfactant or a mixed surfactant. The oil can be derived from a tree, such as the Neem Tree.

DESCRIPTION OF THE INVENTION

The invention reports a simple and efficient process for producing an oil-in-water microemulsion of oils, such as Neem Oil. A microemulsion concentrate may also be prepared that upon dilution in water yields the desired oil-in-water microemulsion concentration. Neem Oil microemulsions formed have a virtually infinite shelf life due to inherent high thermodynamic stability. Also, Neem Oil microemulsions can be formed spontaneously without the help of high shear equipment. Neem Oil microemulsions have been shown to be isotropic, clear and conveniently formed into low viscosity dispersion systems.

Microemulsions can be formed from oils of plant origin such as Neem Oil, petroleum based oils, or with virtually any other oil. The invention preferably employs an FDA approved single surfactant and does not require a cosurfactant. As used herein, the term "single surfactant" refers to one or more of a plurality of species contained within a designated class of surfactant. For example, if the designated class of surfactant is alkyl phenol ethoxylates, wherein the alkyl group has 8 to 12 carbons, a surfactant containing octyl phenol ethoxylates or nonyl phenol ethoxylates is considered herein to constitute a single surfactant.

The invention can form isotropic, non-alcoholic and transparent oil microemulsions. As used herein, the definition of an alcohol is limited to being a carbon chain having 1 to 6 carbons including a substituted OH group, or a non substituted phenyl group ($C_6H_5OH$). Thus, as used herein, a substituted phenol, such an alkyl phenol ethoxylate, is not considered to be an alcohol.

The invention is particularly advantageous by permitting microemulsion formation without the use of a cosurfactant. In other words, an alcohol free microemulsion can be formed. Alcohol free microemulsions are in great demand, particularly in the pharmaceutical and agrochemical industries. Further, nano-sized oil droplets formed using the invention in the range of 1–100 nm are expected to enhance the potency of the oil though improved absorption rates.

Oil-in-water microemulsions may contain from 0.001 to 50.0% oil, by weight of the final product (w/wf). Preferably, the oil-in-water microemulsions have 0.01 to 5% oil, or 5 to 15% w/wf in the case of a microemulsion concentrate.

The single alcohol free surfactant is selected from the group of non-ionic ethoxylated surfactants. In the preferred embodiment, the single surfactant is selected from the group of alkyl phenol ethoxylates having 8 to 12 carbons and an average of 4 to 12 ethoxylate groups. For example, the structure of a nonyl phenol ethoxylate having 8 ethoxylate groups is shown below: $CH_3-CH2-CH_2-CH_2-CH_2-CH_2-CH_2-CH_2-CH_2-C_6H_4-(O-CH_2-CH_2)_8-OH$ Most preferably, the single surfactant is a nonyl phenol ethoxylate containing an average of 4 to 12 ethoxylate groups.

Mixed surfactant systems can be formed by mixing a non-ionic ethoxylated surfactant with at least one of the various ionic surfactants, such as alkyl benzene sulfonates. Other useful ionic surfactants include alkyl benzene carboxylates, alkyl benzene phosphates and alkyl benzene amines. For ready to use product, surfactants are used in concentrations of 0.001 to 40% w/wf, preferably 0.003 to 25% w/wf. In the case of a concentrate, 15 to 60% surfactant w/wf is preferred.

The surfactant to oil ratio should be maintained at a 3:1 weight ratio of surfactant to oil or above. Preferably, the surfactant to oil ratio should be maintained at 4:1 or above. Thus, to prepare a 0.2% w/wf Neem Oil microemulsion, the surfactant level in the microemulsion may preferably be maintained at 0.8% w/wf or above.

To prepare the microemulsion, the required amounts of the oil, surfactant and water are mixed together until a clear transparent microemulsion is formed. Mixing can be supplemented by stirring with need based heating, sonicating or other blending methods known in the art, if it is desired to accelerate the formation of the microemulsion from an otherwise diffusion controlled process.

Similarly, oil microemulsion concentrates, such as Neem Oil microemulsion concentrates can be formed. For example, to prepare a 10% Neem Oil microemulsion concentrate, 10 grams of the oil, 40 grams of the surfactant and water are blended together to form a nearly clear, mass. When diluted in water, this concentrate results in the formation of a stable, clear, and transparent microemulsion of the desired strength. The microemulsion concentrate may be conveniently diluted employing water including standard hard water (hardness 342 parts per million as calcium carbonate) without any adverse measurable effect on the quality and stability of the obtained ready to use microemulsion. Likewise, ready to use microemulsion can be prepared directly by employing standard hard water. The microemulsion concentrate as well as the ready to use microemulsion are stable at temperatures above and below room temperature.

The disclosed non-ionic ethoxylated surfactants can be used to form single surfactant microemulsion of other oils. For example, microemulsions of vegetable oils, such as soybean oil can be formed. In addition, microemulsions of petroleum based oils, such as mineral oil can also be formed using the surfactants disclosed in the invention.

Neem Oil-in-water microemulsions can be used for use in various personal care products such as cosmetics, toiletries, as well as paints and varnishes, agrochemicals, medical and public health products, pesticides and other fields. In particular, Neem microemulsions are particularly well suited for use as skin care and cure products, dentrifice and mouth wash, hand lotions and fertilizer coats. As a pesticide, Neem Oil microemulsions can be particularly effective in controlling cockroaches, mosquitos, houseflies, aphids, moths, spiders and lice.

Neem Oil microemulsions can also be used as a wood treatment to deter termites. Once the microemulsion is absorbed into wood, the wood can be expected to be protected from termites for many years. Enhanced termite protection may be possible using pressure treatment techniques known in the art.

EXAMPLES

Preparation of a Neem Oil Microemulsion Concentrate: 20 grams of Neem Oil, 80.0 grams of a nonylphenol ethoxylate and sufficient water to total 200 grams were blended until a nearly clear microemulsion concentrate was formed. The concentrate formed contained 10.0% Neem Oil and 40% emulsifier. 2.0 grams of this concentrate were diluted with tap water or with standard hard water (hardness 342 parts per million as calcium carbonate) to a final weight of 100 grams. With slight manual shaking, a 0.2% ready to use, clear, transparent Neem Oil microemulsion was produced.

The Neem Oil microemulsion concentrate having viscosity of approximately 1354 centipoise formed was found to be stable to low temperature (~6° C.) and high temperature (54±2° C.) over a two week period tested. At low temperatures, the microemulsion concentrate turns into a thick mass which returns back to its original consistency at room temperature (21–22° C.). At 54±2° C., the microemulsion concentrate tended to be more clear. After 7 days, a thick mass was seen at the surface of the sample which disappeared upon slight shaking by hand. At the end of the heat storage period of over 14 days at 54±2° C. (2 years equivalent shelf life), the microemulsion concentrate remained stable, able to form a ready to use Neem Oil microemulsion upon dilution. Translucence was sometimes noticed in the microemulsions obtained while using the aged samples. This can be overcome by employing lukewarm water during dilution.

Direct preparation of a ready to use Neem Oil Microemulsion: 0.4 grams of Neem Oil, 2.0 grams of nonylphenol ethoxylate and water to make a total of 200 grams were blended until a microemulsion was formed. The mixture produced a clear, transparent microemulsion containing 0.2% of Neem Oil (w/wf).

The quality of the microemulsion formed either by the direct blending of the ingredients or on dilution of the microemulsion concentrate was characterized as having 8.8 nm effective diameter oil droplets, surface tension of 31 dynes $cm^{-1}$ and viscosity of 1.72 centipoise. The microemulsion droplets remained stable between 3.2–3.6 nephelometer turbidity units (NTU) for 72 hours when evaluated using a programmed turbidimeter.

While the preferred embodiments of the invention have been illustrated and described, it will be clear that the invention is not so limited. Numerous modifications, changes, variations, substitutions and equivalents will occur to those skilled in the art without departing from the spirit and scope of the present invention.

What is claimed is:

1. An oil in water microemulsion comprising:
   at least one surfactant selected from the group consisting of non-ionic alkyl phenol ethoxylated surfactants; and
   a plurality of oil droplets comprising at least one oil including Neem Oil, wherein said microemulsion is primary short chain ($C_1$ to $C_6$) alcohol-free, ionic cosurfactant-free and stable upon dilution.

2. The oil in water microemulsion of claim 1, wherein said microemulsion is optically clear.

3. The oil in water microemulsion of claim 1, wherein said oil concentration varies from 5 to 15%, weight by weight of said microemulsion (w/wf).

4. An oil in water microemulsion comprising:
   a single surfactant selected from the group consisting of non-ionic alkyl phenol ethoxylated surfactants; and
   a plurality of oil droplets comprising at least one oil in said water, said oil selected from the group consisting of Neem Oil and vegetable oils, wherein said microemulsion is primary short chain ($C_1$ to $C_6$) alcohol-free, ionic cosurfactant-free and stable upon dilution.

5. The oil in water microemulsion of claim 4, wherein said single surfactant is a nonyl phenol ethoxylate.

6. The method of forming an oil in water microemulsion, comprising:
   providing water, at least one surfactant selected from the group consisting of non-ionic alkyl phenol ethoxylated surfactants, and at least one oil including Neem Oil; and
   mixing said surfactant, said oil and said water to form an oil-in-water microemulsion, wherein said microemulsion is primary short chain ($C_1$ to $C_6$) alcohol-free, ionic cosurfactant-free and stable upon dilution.

7. The method of forming an oil in water microemulsion of claim 6, wherein said at least one surfactant consists of a single surfactant.

8. The method of forming an oil in water microemulsion of claim 7, wherein said single surfactant consists of a nonyl phenol ethoxylate.

9. The method of forming an oil in water microemulsion of claim 6, wherein said oil concentration varies from 5 to 15%, w/wf, whereby a concentrate is formed.

10. The method of forming an oil in water microemulsion of claim 9, wherein said surfactant totals 15 to 60% w/wf.

11. A method of forming an oil in water microemulsion comprising:
   providing water, a single surfactant selected from the group consisting of non-ionic alkyl phenol ethoxylated surfactants, and at least one oil selected from the group consisting of Neem Oil and vegetable oils; and
   mixing said surfactant, said oil and said water to form an oil-in-water microemulsion, wherein said microemulsion is primary short chain ($C_1$ to $C_6$) alcohol-free, ionic cosurfactant-free and stable upon dilution.

12. The method of forming an oil in water microemulsion of claim 11, wherein said oil varies from 0.001 to 5% weight by weight of said microemulsion (w/wf).

13. A method of using a Neem Oil microemulsion, comprising the steps of:
   providing an oil in water microemulsion including water, at least one surfactant selected from the group consisting of non-ionic alkyl phenol ethoxylated surfactants, and Neem Oil, wherein said microemulsion is primary short chain ($C_1$ to $C_6$) alcohol-free, ionic cosurfactant-free and stable upon dilution, and using said microemulsion for at least one use selected from the group consisting of topical applications of said microemulsion in cosmetics, toiletries, agrochemicals or pesticides, blendings of said microemulsion with paints, varnishes or medicines and oral applications of said microemulsion in medicines.

14. The method of claim 13, wherein said surfactant consists of a single surfactant.

15. The method of claim 14, wherein said single surfactant is a nonyl phenol ethoxylate.

* * * * *